United States Patent [19]

Bonnet

[11] 4,237,871
[45] Dec. 9, 1980

[54] DEVICES FOR INJECTING PASTES OR FLUIDS INTO THE HUMAN BODY

[75] Inventor: Ludwig Bonnet, Knittlingen, Fed. Rep. of Germany

[73] Assignee: Richard Wolf GmbH, Knittlingen, Fed. Rep. of Germany

[21] Appl. No.: 69,936

[22] Filed: Aug. 27, 1979

[30] Foreign Application Priority Data

Sep. 20, 1978 [DE] Fed. Rep. of Germany ... 7827905[U]

[51] Int. Cl.³ ............................................. A61B 1/00
[52] U.S. Cl. ......................................... 128/4; 128/216
[58] Field of Search .................... 128/234, 216, 4, 6, 128/8–11, 303 R

[56] References Cited

U.S. PATENT DOCUMENTS

| | | | |
|---|---|---|---|
| 3,830,225 | 8/1974 | Shinnick | 128/4 X |
| 3,960,143 | 6/1976 | Terada | 128/4 |
| 3,980,078 | 9/1976 | Tominaga | 128/4 |

*Primary Examiner*—John D. Yasko
*Attorney, Agent, or Firm*—Kinzer, Plyer, Dorn & McEachran

[57] ABSTRACT

This invention relates to devices for injecting pastes or fluid substances into human obturation organs or sphincters by means of an injection tube which is axially displaceable through an endoscope shaft combined with an optical system and is provided with a distal cannular, and which proximally with respect to the connector member, joining the same to the endoscope stem is connected to a head, which is displaceable on a proximal reinforcing sleeve traversed by said optical system, and is chargeable with paste.

According to the invention a cylinder which is arranged to be filled with material to be injected is connected to the injection tube. A piston is screwable into the open proximal extremity of the cylinder and this piston is provided with external handle means, specifically a head wheel, and the cylinder is joined to the displaceable head.

4 Claims, 3 Drawing Figures

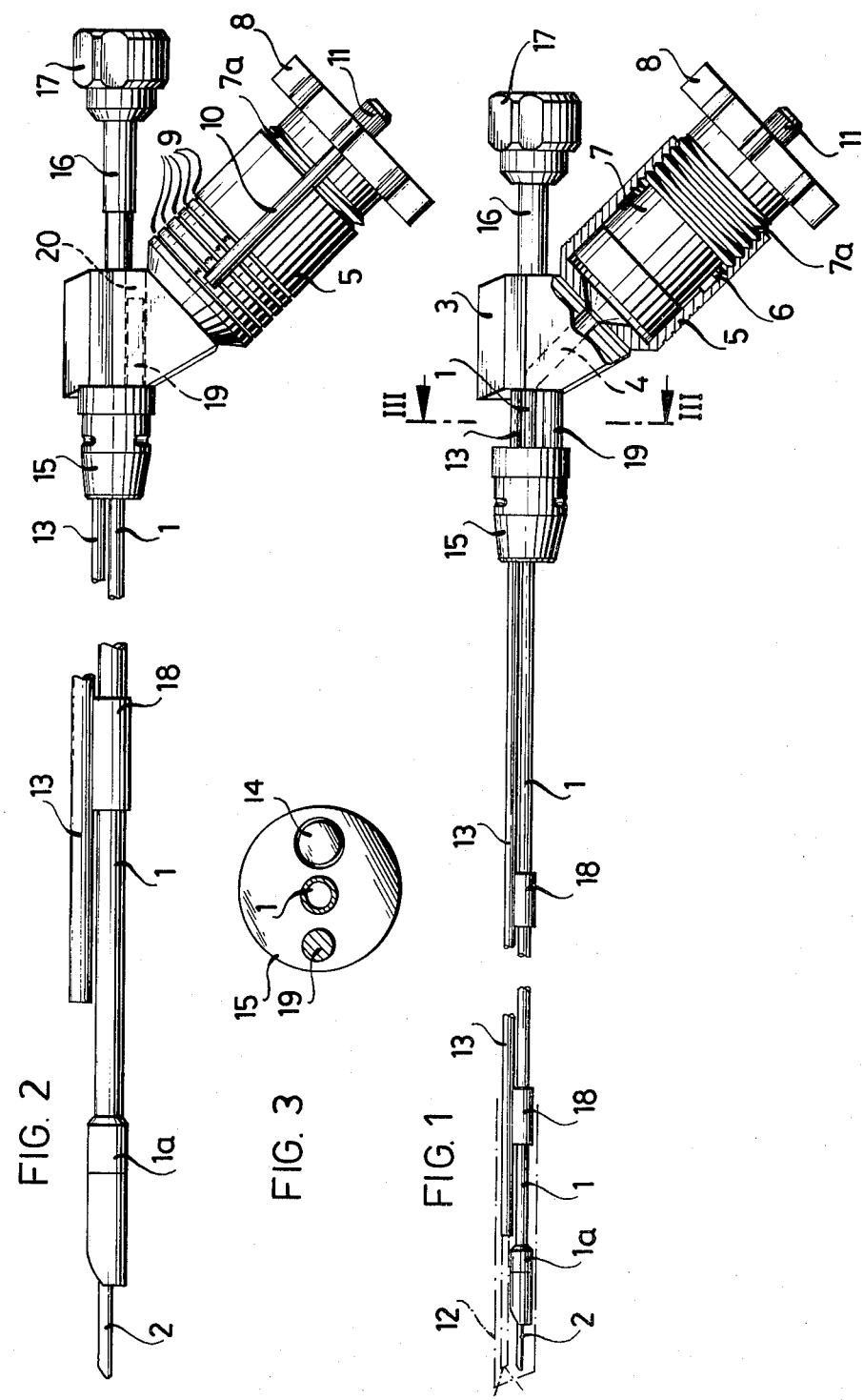

DEVICES FOR INJECTING PASTES OR FLUIDS INTO THE HUMAN BODY

BACKGROUND OF THE INVENTION

The present invention relates to devices for injecting pastes or fluid substances into human obturation organs or sphincters by means of an injection tube which is axially displaceable through an endoscope stem combined with an optical system and is provided with a distal cannula, and which, proximally with respect to the connector, is connected to a head which is displaceable on a proximal reinforcing sleeve traversed by the optical system and may be filled with the material to be injected.

Human obturation organs or sphincters, e.g. vocal chords or urethral obturators, occasionally display the pathological symptoms of an inadequate seal. For this reason, pastes or fluid substances which are not absorbed or absorbed only after a protracted period have already been injected satisfactorily into the obturator organ or the like for a considerable period, to accomplish a tightening-up and volumetric enlargement of the obturator system and thereby an adequate seal. The paste or other material was injected by means of a conventional medical syringe, using a sufficiently long injection tube, but it was learned that a substantial pressure has to be exerted on the syringe piston by the doctor to force thick paste through the long injection tube so as to be able to inject it.

A procedure has already been applied moreover, wherein in the case of injection devices as hereinabove referred to, a housing joined to the injection pipe was connected to the head, into which housing a tube containing paste or fluid may be inserted and wherein it may be rolled up so that it may be discharged via the injection pipe. It was observed that the rolling-up pressure to be applied for this purpose could result in bursting the tube in particular circumstances.

It is an object of the invention to provide an injecting device of the kind referred to but without its attendant disadvantages.

SUMMARY OF THE INVENTION

Accordingly, in a device of this kind, the invention consists in that a cylinder which is fillable with the material to be injected, is connected to said injection tube and into whose open proximal extremity a piston is screwable said piston being provided with external handle means, and said cylinder being joined to said displaceable head.

Although this solution renders it necessary to force the paste or fluid out of a tube into the initially open cylinder, it may then be impelled out of the cylinder and through the injection tube and the thin cannula into the organ in question by comparatively easy displacement by a simple screwing action on the inserted piston provided with the external handle.

BRIEF DESCRIPTION OF THE DRAWINGS

In order that the invention may be more clearly understood, reference will now be made to the accompanying drawings which show one embodiment thereof by way of example and in which:

FIG. 1 shows a partially cross-section side view of an injection device in accordance with the invention, comprising an optical system and an endoscope shaft shown in dash-dotted lines, FIG. 2 shows a similar side view with the distal side enlarged and with the piston screwed in and with a forwardly displaced injection tube and penetrating cannula, and FIG. 3 shows an enlarged cross-section along the line III—III of FIG. 1.

DETAILED DESCRIPTION OF PREFERRED EMBODIMENT

Referring now to the drawings, the device for injection of pastes or the like shown therein comprises a sufficiently long injection tube 1 which in accordance with the invention however comprises a cannula 2 screwable into a distal terminal enlargement 1a, so that the same may be unscrewed after use and cleaned satisfactorily, as may the injection tube 1. The tube 1 is firmly joined at the proximal end to a head 3 through which the injection tube 1 is connected via a bore 4 to an obliquely downwardly directed cylinder 5 secured to the head 3. A piston 7 comprising an external screw-thread may be screwed by means of an external handle in the form of a wheel 8 into the cylinder 5 which is provided with an internal screw-thread 6 for this purpose. At the extremity of the cylinder facing towards the head 3, a number—e.g. five—of circumferential grooves 9 is cut into the external circumference, and those are numbered. Upon screwing the piston 7 into the cylinder 5 by means of the wheel 8, a pin 10 axially parallel to the cylinder and firmly joined to the wheel 8 travels along the external periphery of the cylinder so that its free extremity indicates, by co-ordination with the engraved grooves 9, how much paste etc. had been injected. The cylinder and the screw-thread are so dimensioned that the groove spacing corresponds to one revolution of the piston and for example 1 cc of paste. So that the doctor may easily determine the quantity of paste injected upon operating the instrument as a whole, apart from and even without the verification by means of the groove markings, the indicator pin 10 has a milled head 11 at its proximal extension at the outer surface of the wheel 8, whereby he may count the revolutions during injection under optical examination. The injection device is combined with an endoscope to prevent injuries upon insertion into body cavities. A wholly round internal guide tube 13 for the optical system 14 is joined via a connector 15 to the external shaft 12 shown dash-dotted at the far side, the guide tube 13 traversing the connector 15 and opening proximally into a reinforcing tube 16, and both terminating in a connector 17 for the optical system 14 and being firmly connected to the same.

Proximally with respect to the connector 15, the guide tube 13 for the optical system is provided with an enlargement 16 comprising the optical connector 17, the block 3 joined to the cylinder 5 and to the injection tube 1 displaceable through the connector 15 being displaceable axially between said enlargement 16 and the connector 15. The injection tube 1 is also guided by means of sleeves 18 secured on the optical guide tube 13. At the near side, the connector 15 is provided with a guide pin 19 displaceably engaging in a guideway 20 of the block 3, whereby the guide tube 13 is relieved of the unilateral paste pressure.

In the idle position shown in FIG. 1, the cannula 2 is situated inside the external shaft 12 and, in this position, the endoscope containing the injection tube 1 and the cannula 2 is offered up under observation to the obturation organ or the like within a body cavity, and the injection tube 1 together with the cannula is then extruded out of the stem 12 by outward displacement of the block 3 and the cannula 2 is inserted into the organ under observation. The paste is thereupon wholly or partially forced out the cylinder 5 and injected into the organ via the injection tube and the cannula by screwing the piston 7.

I claim:

1. In a device for injecting pastes or fluid substances into human obturation organs or sphincters by means of an injection tube which is axially displaceable through an endoscope shaft combined with an optical system and is provided with a distal cannular, and which, proximally with respect to the connector member, joining the same to the endoscope stem is connected to a head, which is displaceable on a proximal reinforcing sleeve traversed by said optical system, and is chargeable with paste, the invention which consists in that a cylinder which is fillable with the material to be injected, is connected to said injection tube and into whose open proximal extremity a piston is screwable, said piston being provided with external handle means and said cylinder being joined to said displaceable head.

2. A device according to claim 1, wherein said handle means of said piston which is displaceable in said cylinder, is connected to an outer indicator pin extending parallel to said cylinder, the free extremity of said pin being co-ordinadable with markings located around the circumference of said cylinder.

3. A device according to claim 1, wherein said connector member for said endoscope shaft is firmly joined proximally to a guide pin located parallel to the longitudinal axis of the device, said guide pin being engageable in a guide of said axially displaceable head.

4. A device according to claim 1, wherein said distal cannula of said injection tube is releasably connected to said injection tube.

* * * * *